United States Patent [19]

Linnau

[11] Patent Number: 5,393,666
[45] Date of Patent: Feb. 28, 1995

[54] METHOD OF ACTIVATING PROTHROMBIN

[75] Inventor: Yendra Linnau, Vienna, Austria

[73] Assignee: Immuno Aktiengesellschaft, Vienna, Austria

[21] Appl. No.: 34,778

[22] Filed: Mar. 19, 1993

[30] Foreign Application Priority Data

Apr. 6, 1992 [AT] Austria ................. 713/92

[51] Int. Cl.$^6$ ............... C12N 11/00; C12N 11/16; C12N 9/00; A61K 37/547
[52] U.S. Cl. ................. 435/183; 435/174; 424/94.64
[58] Field of Search ............ 435/183, 213, 179, 174; 424/94.64; 530/384

[56] References Cited

U.S. PATENT DOCUMENTS

| | | | |
|---|---|---|---|
| 4,334,018 | 6/1982 | Kirchhof | 435/13 |
| 4,610,962 | 9/1986 | Takagi et al. | 435/179 |

FOREIGN PATENT DOCUMENTS

| | | |
|---|---|---|
| 385657 | 5/1988 | Austria. |
| 0120835 | 3/1984 | European Pat. Off. . |
| 0247998 | 2/1987 | European Pat. Off. . |
| 0294851 | 12/1988 | European Pat. Off. . |

OTHER PUBLICATIONS

Bajaj, S. P. et al. "The Journal of Biological Chemistry," vol. 248 (22), Nov. 25, 1973, pp. 7729–7741.
Heldebrant, C. M., et al., "The Journal of Biological Chemistry," vol. 248 (10), May 25, 1973, pp. 3642–3652.
Van de Graaff, et al., *Concepts of Human Anatomy and Physiology*, pp. 712–713, 1986 WCB Publishers.
Rimon, A., et al., "Biochemistry," vol. 5 (2), Dubuque, Iowa Feb. 1966, pp. 792–798.
Radcliffe, R. D., et al., "The Journal of Biological Chemistry," vol. 248 (19), Oct. 10, 1973, pp. 6788–6795.
Fujikawa, K. et al., "Biochemistry," vol. 13 (26), 1974, pp. 5290–5299.
Papahadjopoulos, P., et al., "Biochemistry," vol. 3 (12), Dec. 1964, pp. 1931–1939.
Pechet, L., et al., "Federation Proc.," vol. 19, Mar. 1960, p. 64, #2–abstract.
Kisiel, W., et al., "Biochim. et Biophys. Acta." vol. 329, 1973, pp. 221–232.
Aldrich, F. L. et al., "Federation Proc." vol. 17, Mar. 1958, p. 179, #704–abstract.
Alexander, B., et al., "Proc. of the VIIIth Congress of European Soc. of Hematol.," vol. 2, 1962 #404.
Eagle, H. et al., "The J. of Gen. Physiology," vol. 20, 1937, pp. 543–560.
Derwent Abstract (SU–A–994,556).
Derwent Abstract (DD–A–137 325).
Zubairov et al., *Voprosy Meditsinskoi Khimii* (1976) pp. 187–191 (English translation).
American Journal of Physiology (1961), 201(2), pp. 298–302.
Fandaburu et al., "Prothrombin Activation With Trypsin As Enzyme," *Am. J. Physical*, vol. 201:298–302, (1961).
Zubairov et al., "Vosprosy Meditsinskoi Khimii 0043.260000," pp. 187–191, (1976) abs.
Miletich et al., "The Synthesis Of Sulfated Dextran Beads For Isolation Of Human Plasma Coagulation Factors II, IX, and X$^1$," *Analytical Biochemistry*, vol. 105:304–310, (1980).
Kisiel et al., "The Action Of Factor Xa. Thrombin And Trypsin On Human Factor II," *Biochimica et biophysica Acta*, vol. 329:221–232, (1973).
Brummelhuis, "Preparation Of The Prothrombin Complex," Methods of Plasma Protein Fractionation, ed. M. Curling, Acad. Press, pp. 117–128, (1980).

*Primary Examiner*—Douglas W. Robinson
*Assistant Examiner*—Kristin Larson
*Attorney, Agent, or Firm*—Foley & Lardner

[57] ABSTRACT

There is disclosed a method of activating prothrombin by means of trypsin, wherein the prothrombin is recovered from a blood or plasma fraction, treated with trypsin immobilized on a water-insoluble carrier, and separated from the immobilized trypsin after activation.

4 Claims, No Drawings

METHOD OF ACTIVATING PROTHROMBIN

The invention relates to a method of activating blood coagulation factors by means of trypsin as well as to the use of the method for producing thrombin.

Blood coagulation is subject to a series of sequential reactions, in which blood coagulation factors are activated, which, in turn, catalyze subsequent reactions. Finally, fibrin is formed from fibrinogen by the action of activated prothrombin (thrombin). The activation of blood coagulation factors in most cases involves proteolysis of a zymogen to yield a proteolytically active enzyme. The mechanism of this activation reaction still is partially unknown, for which reason in vitro activation of blood coagulation factors is difficult to control. For instance, the conversion of prothrombin into thrombin occurs very slowly by means of factor Xa and calcium alone. Its optimum progression is ensured only in the presence of a complex of several factors (prothrombinase complex). In addition to factor Xa, factor V, phospholipids and calcium belong to this complex. Factor Xa proteolytically cleaves the prothrombin molecule (molecular weight 68,000 D), thus generating the active enzyme thrombin (molecular weight 30,000 D).

The plasma protease thrombin is a multifunctional enzyme which not only is coagulatively active on account of fibrinogen being cleaved to fibrin, but, inter alia, also activates coagulation factors V, VIII and XIII and cleaves its own proenzyme (prothrombin). In therapy, thrombin is used either alone or together with fibrinogen to stop bleedings or, in surgery, to adhere tissues.

The activation of prothrombin via the prothrombinase complex is difficult to imitate in vitro, for which reason attemps have been made to generate thrombin under the action of proteases of human or animal origin.

Assays on the activation of human prothrombin by bovine factor Xa or bovine trypsin have demonstrated that the activation by trypsin via the same physiologic intermediates takes place in the same way as by factor Xa. However, the yield is 50% at the most, since proteolysis goes on in case of trypsin, resulting in the degradation of thrombin and in the formation of low molecular weight products (Kisiel and Hanahan (1973), Biochim. Biophys. Acta 329, 221–232).

The yield of thrombin may be improved by additives, such as serum albumin or high concentrations of glycerol (50%) (Landaburu et al. (1961), Am. J. Physiol. 201, 298–302). Yet, the product must be purified from trypsin and the various additives after the activation reaction in a cumbersome manner before being processed to a biologically compatible preparation.

The elimination of trypsin from the reaction medium could be substantially simplified by the use of immobilized enzyme. However, the use of immobilized trypsin for the activation of prothrombin hitherto has been considered impossible. Assays have proved that immobilized trypsin, as opposed to soluble trypsin, is not suitable for the activation of prothrombin to thrombin in citrated plasma (Zubairov and Zinkevich (1976), Vosprosy meditsinskoi khimii 22(2), 187–91).

The present invention is based on the object to provide a simple method of activating blood coagulation factors, which guarantees a high yield of activated enzyme without having to carry out cumbersome purification steps after the activation reaction.

In accordance with the invention, this object is achieved by a method of activating blood coagulation factors with trypsin, which consists in that the blood coagulation factor is recovered from a fraction containing prothrombin complex, is treated with trypsin immobilized on a water-insoluble carrier, and the immobilized trypsin is separated after activation of the blood coagulation factor. As water-insoluble carriers, cellulose, dextranes, agarose, acrylates or silicates are, for instance, used.

The method is particularly suited for the activation of the blood coagulation factors prothrombin, factor IX or factor X.

An advantageous embodiment of the invention consists in that the activation of prothrombin, factor IX or factor X is carried out at a pH of 5.8 to 7.9, at a conductivity of 5 to 24 mS and at a temperature of 2° to 45° C.

The method according to the invention is particularly suited for recovering thrombin from prothrombin. The controlled treatment of a fraction containing purified prothrombin with immobilized trypsin comprises the rapid and complete separation of trypsin after a predetermined treatment time. Thus, the product substantially does not contain any cleavage products. The addition of common stabilizers, such as 50% glycerol, may be renounced. The thrombin containing fraction may be processed to a pharmaceutical preparation in a conventional manner.

To produce an activated enzyme from a blood coagulation factor, it is possible to activate either the purified blood coagulation factor or a blood coagulation factor complex, wherein the activated enzyme advantageously is further purified in the latter case. Thus, thrombin may be obtained by the activation of purified prothrombin or of prothrombin complex.

An additional advantage of the invention resides in that, simultaneously with the activation of a blood coagulation factor, virus activity is considerably reduced if a starting product is used that is derived from a virus-contaminated pool.

The virus-inactivating effect of immobilized trypsin in a blood coagulation factor-containing fraction was surprising. Treatment with immobilized neutral hydrolases to inactivate reproductive filterable pathogens merely was known in immunoglobulin-G-containing fractions (EP-A-0 247 998).

It goes without saying that additional measures for the inactivation of possible present infectious agents may be taken within the scope of the method according to the invention. Thus, it is, for instance, possible to perform a vapor-heat treatment at the moistened lyophilized starting material.

The invention will be explained in even more detail by way of the following examples.

1. Immobilization of trypsin 1.2 g trypsin type III (Sigma, article No. T 8253) were bound to 350 ml (100 g powder) of CNBr-activated SEPHAROSE 4B according to the manufacturer's instructions (Pharmacia). More than 90% of the trypsin was immobilized.

2. Activation of prothrombin in a prothrombin-complex-containing fraction

From 50 l human cryoprecipitate-poor blood plasma, the prothrombin complex was isolated according to the known method of Brummelhuis in "Methods of Plasma Fractionation" (J. M. Curling ed., Acad. Press 1980) by adsorption on an anion exchanger. The salt concentration of the prothrombin-containing fraction was reduced to 150 mM NaCl by diafiltration and the product was freezedried.

In order to inactivate possibly present pathogens, the fraction was heated to 60° C. for 10 hours and to 80° C. for 1 hour in the presence of water vapor according to AT-B-385,657.

The heated bulk powder was dissolved to 25 U prothrombin/ml (protein concentration 12 mg/ml) and was treated with 1 ml trypsin immobilized on SEPHAROSE, for 150 min at 25° C. under slow stirring. The thrombin activity was 1980 U per ml, the specific activity was 165 U/mg protein.

3. Further purification of the thrombin from 2.

The thrombin was produced according to 2. and further purified over a 45 ml S-SEPHAROSE column (Pharmacia) in the following manner. The column was equilibrated with 25 mM $Na_3$ citrate pH 6.2. Thrombin (105,000 U in 25 mM $Na_3$ citrate) was bound to the S-Sepharose, washed with the same buffer and eluted with 150 ml of a 450 mM NaCl solution.

The yield of thrombin was 94%, the specific activity was 1735 U/mg protein. This thrombin was capable of being freezedried in the presence of 9 g/l NaCl and 5 g/l glycine to yield a stable preparation.

4. Activation of purified prothrombin

The recovery of the vapor-treated prothrombin complex from the plasma was carried out according to 2.

In addition to prothrombin, the virus-inactivated product contained factor IX and factor X. By chromatographic separation over sulfated SEPHADEX G50 (Pharmacia) (Miletich et al., (1980), Analyt. Biochem. 105, 304–310), factors IX and X were separated from prothrombin. After activation of the purified prothrombin to thrombin according to 2, the specific activity was 745 U/mg.

5. Further purification of the thrombin from 4.

110,000 U thrombin were produced according to 4. and were further purified over a 45 ml S-SEPHAROSE column. Upon purification, the thrombin had a specific activity of 3240 U/mg protein.

What I claim is:

1. A method of activating prothrombin comprising the steps of:

providing a blood or plasma fraction containing prothrombin, recovering said prothrombin from said fraction containing prothrombin, contacting said prothrombin with immobilized trypsin to activate said prothrombin, wherein said activation of said prothrombin is carried out at a pH of 5.8 to 7.9, a conductivity of 5 to 25 mS and a temperature of 2° to 45° C. and whereby thrombin is formed, and separating said immobilized trypsin after the formation of said thrombin.

2. A method for activating prothrombin to form thrombin, comprising the step of contacting said prothrombin with immobilized trypsin wherein said contacting occurs at a pH of 5.8 to 7.9, a conductivity of 5 to 25 mS and a temperature of 2° to 45° C.

3. A method according to claim 2, wherein said method does not require the addition of stabilizers.

4. A method according to claim 2, wherein said thrombin is treated to inactivate any virus present.

* * * * *